(12) United States Patent
Cesaro et al.

(10) Patent No.: US 6,911,475 B1
(45) Date of Patent: Jun. 28, 2005

(54) USE OF NICOTINE OR ITS DERIVATIVES IN A DRUG FOR TREATING NEUROLOGICAL DISEASE, IN PARTICULAR PARKINSON'S DISEASE

(75) Inventors: Pierre Cesaro, Saint-Maurice (FR); Gabriel Villafane, Paris (FR)

(73) Assignee: Assistance Publique-Hopitaux de Paris (FR)

( * ) Notice: Subject to any disclaimer, the term of this patent is extended or adjusted under 35 U.S.C. 154(b) by 0 days.

(21) Appl. No.: 09/653,717

(22) Filed: Sep. 1, 2000

(30) Foreign Application Priority Data

Sep. 2, 1999 (FR) .............................. 99 11029

(51) Int. Cl.[7] ...................... A61K 31/195; A61K 31/44; A61K 31/495; A61K 31/50; A61K 31/445
(52) U.S. Cl. ...................... 514/567; 514/343; 514/250; 514/319
(58) Field of Search ................ 514/567, 343, 514/250, 319

(56) References Cited

U.S. PATENT DOCUMENTS 5,232,933 A     8/1993    Lippiello et al. ........... 514/343
5,242,935 A     9/1993    Lippiello et al. ........... 514/343

OTHER PUBLICATIONS

Medline AN 86017126, Lieberman et al, Pharmacological Reviews, 1985 Jun. 37(2) 217–27, abstract.*
A.M. Janson, et al./Brain Research (1994) 655: 25–32.
Trends Neurosciences, Olanow, C.W., et al., (1996) 19: p. 102–109.
E. F. Domino et al; Nicotine Alone and in Combination with L–DOPA Methyl Ester . . . vol. 158 (1999) p. 414–421.
Pharmacology of Nicotine and its Therapeutic Use in Smoking, David J. K. Balfour, et al., (1996) 72: vol. 1: 51–81.
J. Doyon et al., M Medecine et Science (1999), 5:XIX–XXIII and English Translation of same p. 1–6.

* cited by examiner

*Primary Examiner*—Rebecca Cook
(74) *Attorney, Agent, or Firm*—Lerner, David, Littenberg, Krumholz & Mentlik, LLP

(57) ABSTRACT

The present invention concerns the use of nicotine or a derivative thereof for producing a drug for continuous or progressive administration of 0.2 mg to 5 mg per day per kilogram of body weight in man, said drug being administered simultaneously with L-DOPA in a dose at least 30% lower than the effective dose when L-DOPA is administered alone.

29 Claims, 2 Drawing Sheets

USE OF NICOTINE OR ITS DERIVATIVES IN A DRUG FOR TREATING NEUROLOGICAL DISEASE, IN PARTICULAR PARKINSON'S DISEASE

The present invention relates to the use of nicotine derivatives in producing drugs for the treatment of Parkinson's disease and multi-systematised atrophies.

Parkinson's disease and associated diseases do not have an undisputed definition. This is connected with the fact that the cause is still unknown.

Parkinson's disease is diagnosed by a battery of clinical syndromes which are characterized by motor signs (tremor at rest, rigidity, hypokinesia and postural instability) and neuropsychological deficits which can even affect certain cognitive functions.

Over a number of years, however, other diseases known as multi-systemic atrophies can clinically evolve like Parkinson's disease. Particular examples are striatonigral degeneration, ponto-cerebellar atrophy, or Shy-Drager syndrome.

Receptors play a significant role in Parkinson's disease as they are the site for action of the dopamine liberated by the pre-synoptic element.

D1 receptors are preferentially stimulated by dopamine. They are located on the post-synaptic membrane and are coupled to the adenylate-cyclase activity. They are localised in the striatum, the nucleus accumbens, and the olfactory tubercle.

D2 receptors are preferentially stimulated by certain dopaminergic agonists such as bromocriptine and pyribedil.

A number of studies carried out both in man and in animals have demonstrated that these problems are in a large part due to chronic degeneration of dopaminergic neurones of the nigrostriatal system. The current treatment, which remains the reference treatment, is treatment with L-DOPA accompanied, if necessary, by D2 receptor agonists, such as those cited above. However, that type of treatment has medium to long-term side effects such as dyskinesia.

The problems with such undesirable effects has encouraged research into other therapies, in particular surgical therapy such as a dopaminergic neurone grafts (Olanow, C. W., et al., (1996), Trends Neurosciences 19: 102–109).

The aim of that type of graft is to develop dopaminergic innervation in the striatum which then replaces the faulty innervation in the Parkinson's patient. However, that technique is very expensive and, like any graft, depends on the availability of donor neurones which are generally obtained from a foetus during voluntary abortion. However, it appears that while that graft, when carried out bilaterally in the putamen, can improve bradykinesia, akinesia and rigidity in the Parkinson's patient, it does not have definite effects as regards bradyphrenia and other cognitive functions. In addition to the disadvantages linked to the graft outlined above, that type of treatment does not overcome the problem of treating Parkinson's disease and its different associated symptoms, in particular from the neuropsychological aspect (J. Doyen et al., M Medecine et Science (1999), 5: XIX–XXIII).

It has also been observed that the incidence of Parkinson's disease is significantly lower in smokers than in non smokers. It has been suggested that nicotine has the property of activating nicotinic cholinergic receptors on acute administration and causing an increase in the number of such receptors on chronic administration of nicotine to animals (D. J. K. Balfour et al., Pharmacology and Therapeutics (1996), 72, vol 1: 51–81). However, none of the nicotine treatment trials which have been conducted concerned long-term treatment without interruption. The term "long-term" means a period of more than three months. Further, the development of a treatment associating nicotine or its derivatives, L-DOPA and D2 receptor agonists has never been researched.

The development of a drug, and more generally a treatment, for restoring the functionality of D1 and D2 dopaminergic rectepors remains a major problem in the field of neurodegenerative disease.

The term "nicotine" means both nicotine and its different derivatives from the instant they are capable of coupling with nicotinergic receptors and of being agonists for these receptors. An example which can be cited is nicotine resin complex.

Nicotine derivatives have been described for use in treating Parkinson's disease. Examples which can be cited are United States patents U.S. Pat. Nos. 5,232,933 and 5,242,935. However, those patents do not disclose the administration period and the experiments were carried out on mice or rats. Further, the usual symptoms, whether physical or neuro-psychological symptoms, were not observed. Finally, they are silent as regards simultaneous or separate treatment with L-DOPA and D2 receptor agonists.

A study carried out by A. M. Janson et al., (1994), 655: 25–32 described results of chronic treatment in the rat. The treatment termed "long-term" was also in this case 14 days, which is not comparable with the treatment with the drug of the invention.

The present invention concerns the use of nicotine or a derivative thereof for producing a drug for continuous or progressive administration of 0.2 milligrams (mg) to 5 mg per day per kilogram of body weight in man, said drug being administered simultaneously with L-DOPA in a dose at least 30% lower than the effective dose when L-DOPA is administered alone. A preferred dose is in the range 0.2 to 3 mg per kilogram per 24 hours.

Such a drug is intended to treat neurodegenerative diseases, in particular Parkinson's disease and Tourette's syndrome.

Preferably, the doses of L-DOPA administered simultaneously with the drugs of the invention are at least 50% lower than the effective dose when it is administered alone.

The normal treatment routinely used to treat Parkinson's disease can be constituted by daily administration of 200 mg per day to 1500 mg per day and doses of dopaminergic agonists are completely random and dependent on each dopaminergic agonist.

Considering the secondary effects of medium term treatment with L-DOPA, a reduction in the L-DOPA dose of 30% or 50% or 60% with respect to that dose has distinct advantages.

The drug of the invention is administered in accordance with a protocol which involves a gradual increase in the cumulative doses of nicotine or its derivatives, over three consecutive months, followed by stabilized doses after three months. The increase in the dose of nicotine over the first three to four months is accompanied by a concomitant reduction in the L-DOPA dose as the improvements in parkinsonian syndromes are observed.

By way of example, administration is 0.2 mg per kilo per 24 hours for three to four months, then 1.4 to 1.5 mg per kilo per 24 hours from the third or fourth month then, depending on the improvement in symptoms and the therapeutic needs of the patient, the dose is adjusted to between 2 and 3 mg per kilo per 24 hours.

The present invention also relates to a method for treating neurodegenerative diseases and in particular Parkinson's disease or Tourette's syndrome, comprising long-term administration of nicotine or a derivative thereof in an amount of 0.2 to 5 mg per day per kilogram of body weight in man; this administration is simultaneously accompanied by doses of L-DOPA which are not active when this latter is administered alone. It concerns long-term treatment, i.e., a minimum period of four months and preferably six months, which enables the physical and neuro-psychological symptoms to reduce or even disappear, in a stable manner. The physical symptoms studied were: tremor, axial rigidity, gait and speech. The neuro-psychological symptoms were memory and sexual activity.

Clinical evaluation of the effect of the drug of the invention and of the treatment method was carried out using conventional UPDRS I, II and III neurological tests. These tests enabled both neuro-psychological and physical effects to be measured.

The UPDRS I test measures, on a scale of 0 to 4, mentation, behaviour and mood of the patient, taking into account the criteria of intellectual impairment, thought disorder, depression and motivation/initiative.

The UPDRS II test measures a series of sensory or motor physical tests, also on a scale of 0 to 4.

The UPDRS III test measures the motor activity of the patient, again on a scale of 0 to 4.

Zero indicates a normal state and four indicates maximum perturbation.

It is essential that treatment with the drugs of the invention is a long-term treatment; thus the different modes of administration of this drug must be compatible with this type of treatment. In particular, the drug of the invention can be administered cutaneously using a rapid or slow release patch, or continuously using an extracorporal type pump. A sub-cutaneous catheter can enable the required dose of nicotine to be contantly administered, which is adjustable using a battery-driven variable speed governor.

The drug can also be administered orally, in a galenical form also comprising L-DOPA and/or dopaminergic agonists.

The drug of the invention enables multiplication, stimulation and increase of nicotinergic receptors and pre-synaptic and post-synaptic D1 and D2 receptors in the nigrostriatum zone, which can be shown by positron emission tomography (PET) using F18-DOPA and racloprid respectively, using the technique described in Medecine/Sciences (1999), 15: 490–495.

The example below shows the unexpected advantages of the drug of the invention, administered concomitantly with L-DOPA, and of the method for treating Parkinson's disease and its associated diseases.

EXAMPLE 1

A patient aged 57 years had been treated for 10 years with 800 mg per day of L-DOPA, supplemented by 30 mg per day of bromocriptine.

Over a period of six months, nicotine patches were administered to the patient, firstly using increasing doses over the first three months to reach a dose of 102 mg per day and then by combining two types of patch, namely a patch in the form of a slow release patch (patch P) and rapid release patches (patch R). Each patch P contained 21 mg of nicotine and each patch R contained 15 mg of nicotine. The administration kinetics over the first twelve months are shown in Table I below:

TABLE I

| Month | Patch P | Patch R | Doses R | Total doses/day |
|---|---|---|---|---|
| 1 | 21 mg of nicotine | | | 21 mg |
| 2 | 42 mg of nicotine | | | 42 mg |
| 3 | 63 mg of nicotine | 2 doses | 30 mg (RR) (2 × 15 mg) | 93 mg |
| 4 | 42 mg of nicotine | 4 doses | 60 mg (4 × 15 mg) | 102 mg |
| 5 | 42 mg of nicotine | 4 doses | 60 mg (4 × 15 mg) | 102 mg |
| 6 | 42 mg of nicotine | 4 doses | 60 mg (4 × 15 mg) | 102 mg |
| 7–12 | 42 mg of nicotine | 4 doses | 60 mg (4 × 15 mg) | 102 mg |

Overall, the daily dose was 21 mg the first month and stabilized at 102 mg from the fourth month, divided into 42 mg under slow release and 60 mg under rapid release.

Doses of L-DOPA and Bromocriptine

Concomitantly, L-DOPA was administered in a decreasing dose with time; in contrast, the bromocriptine dose was unchanged and remained at 30 mg per day over the entire treatment, as shown in Table II below.

TABLE II

| MONTH | L-DOPA | Nicotine | Bromocriptine |
|---|---|---|---|
| 1 | 800 | 0 | 30 |
| 2 | 800 | 21 | 30 |
| 3 | 800 | 42 | 30 |
| 4 | 600 | 93 | 30 |
| 5 | 400 | 102 | 30 |
| 6 | 300 | 102 | 30 |
| 7 | 200 | 102 | 30 |
| 8 | 200 | 102 | 30 |

Figure 1:
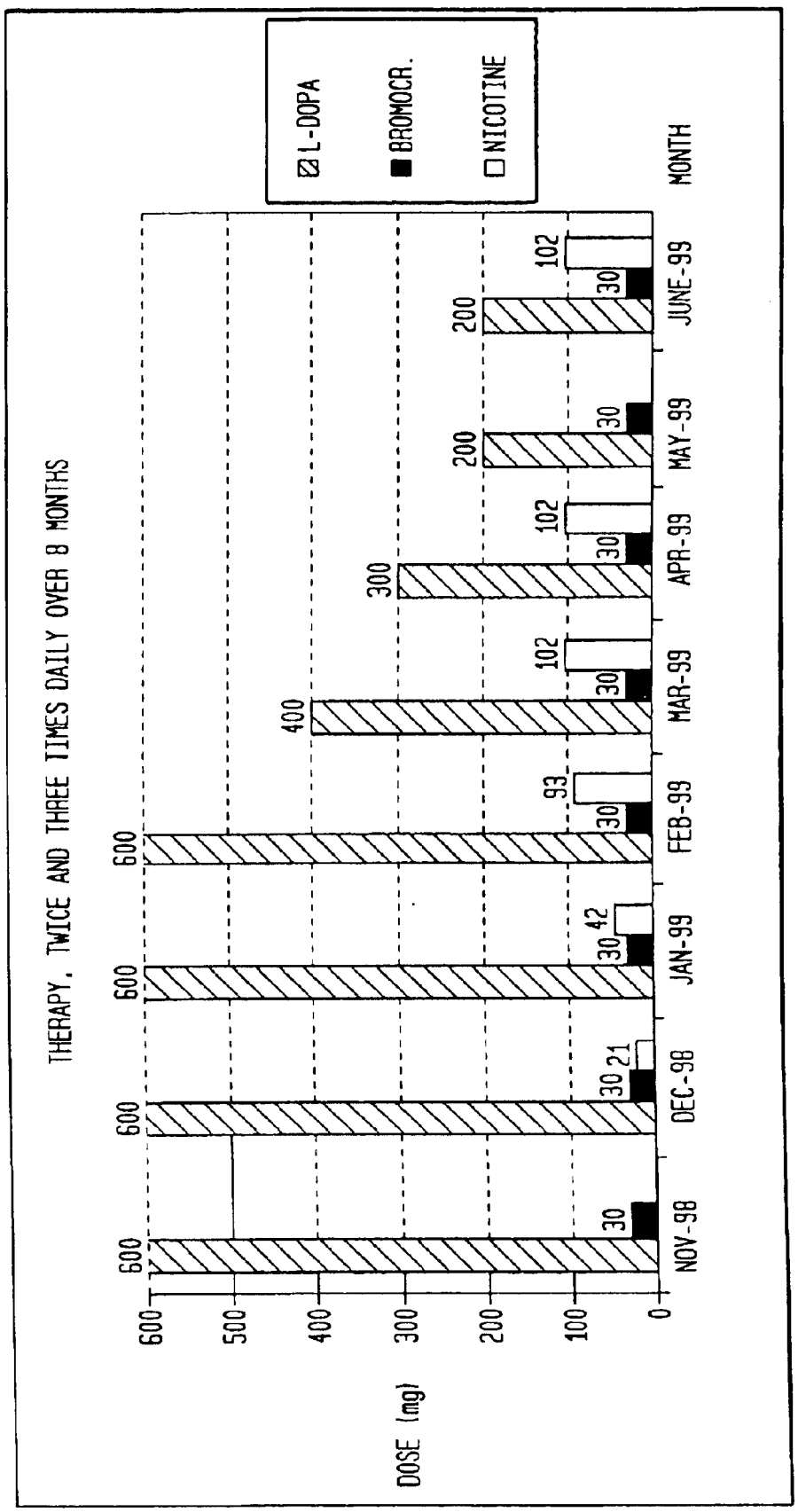
FIG. 1 shows the respective doses of L-DOPA, bromomocriptine and nicotine administered over time, expressed in mg.

FIG. 1 gives an overall view of the treatment with time. Stopping administration of the nicotine in the eighth month had no symptomatic effect.

EXAMPLE 2

Effect of the Drugs of the Invention and Nicotine Treatment on Clinical Manifestations of Parkinson's Disease and Multisystemic Atrophies Clinical evaluation was based on the L-DOPA test and was carried out as follows:

The UPDRS test used is described below.

It consisted of halting the L-DOPA therapy to a zero dose 12 to 24 hours before the test.

The next day, every half hour, the condition and the clinical changes in the patient was measured during stoppage ("off" period, no L-DOPA) then the clinical changes during resumption ("on" period with L-DOPA). The time was measured using a chronometer.

This test serves to:

diagnose Parkinson's disease;

measure the sensitivity to L-DOPA;

establish the choice of treatment to be carried out (graft, electrical stimulation, medical treatment).

This test was carried out with UPDRS measurements as described above:
- motor UPDRS (Unified Parkinson's Disease Rating Scale);
- UPDRS I (mental state of patient);
- UPDRS II (daily life, on-off); ADL (activities of daily living);
- Self-evaluation test (test carried out by the patient, verification and confirmation by physician of fluctuations in on-off periods during the day).

Figure 2:
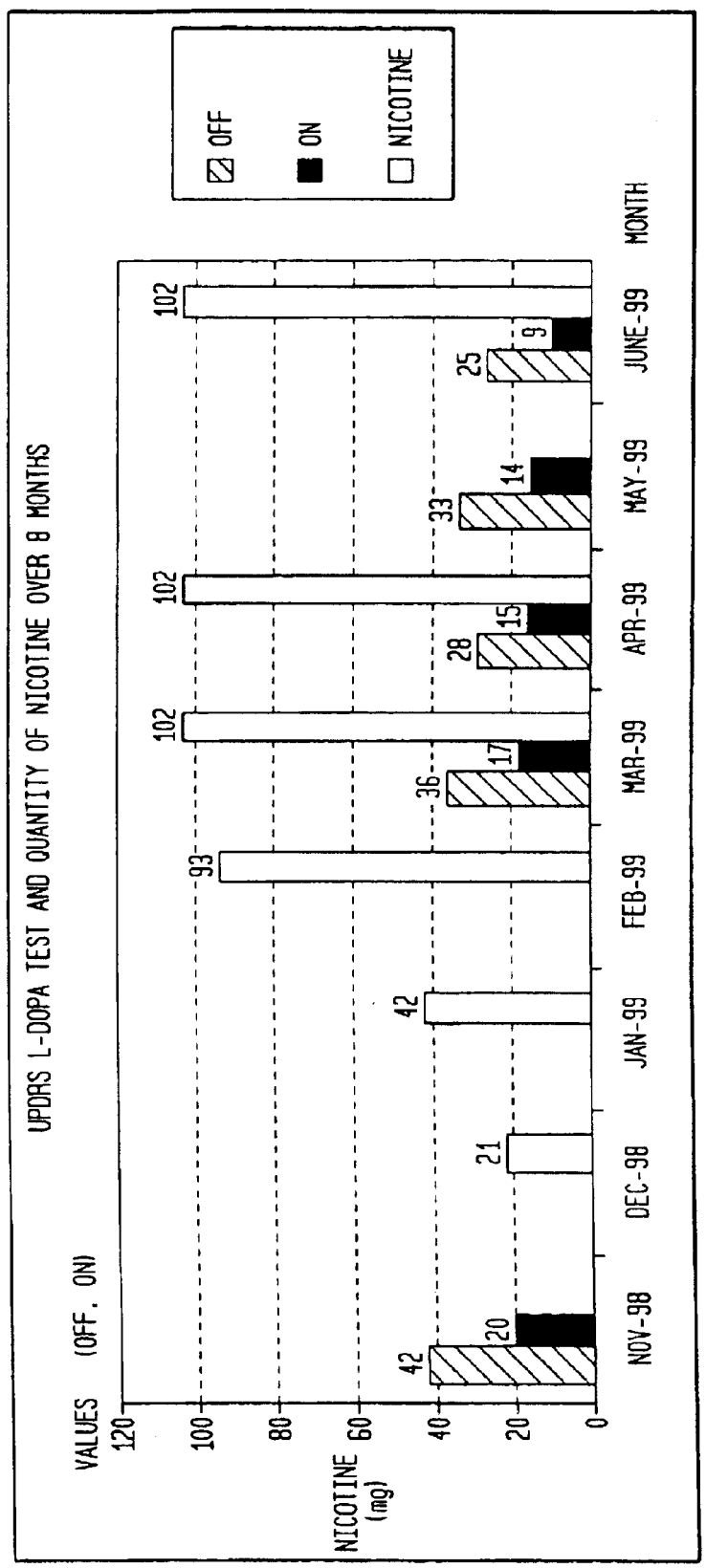
FIG. 2 shows the results of UPDRS tests in the absence of L-DOPA (off) and in the presence of L-DOPA (on). The bars on the histogram show the nicotine dose.

The results of the on-off test for the UPDRS test over the on/off periods are shown in FIG. 2. This Figure shows the respective values of the "off" and "on" periods in the presence of 30 mg of bromocriptine, and in the presence of 250 mg of L-DOPA for the first "on" test and 187.50 mg for the "on" test after six months of treatment. A reduction in the score for the "off" periods can be seen except in the seventh month of treatment due to an interruption in the nicotine treatment at that time. In contrast, the "on" periods showed a constant decrease in UPDRS measurements. These measurements have to be interpreted as the existence of a real long-term curative effect of treatment with the drug of the invention. Further, the patient who had suffered from sexual problems and urinary dysfunction for two years exhibited completely re-established functions after four months of treatment.

Similarly, memory disorders were reduced, along with depressive episodes.

Finally, Tables III and IV below respectively show the effect of treatment on physical manifestations and on motor UPDRS III tests without and with nicotine treatment.

TABLE III

| Aspect | Before nicotine treatment | With nicotine treatment | Without nicotine treatment | Re-administer nicotine at 102 mg/kg/d |
|---|---|---|---|---|
| Tremor | 3 | 1 | 3 | 1 |
| Axial rigidity | 2 | 0 | 1 | 0 |
| Gait | 2 | 0 | 1 | 0 |
| Speech | 2 | 0 | 2 | 0 |

TABLE IV

| Test | Without nicotine treatment (day 0) | With nicotine treatment (6 months later) |
|---|---|---|
| UPDRS I (mental state) | 10 | 0 |
| UPDRS II off (daily activity, ADL) | 22 | 10 |
| UPDRS II on (daily activity, ADL) | 13 | 6 |

It is clear that the treatment completely abolished axial rigidity, and normalised gait and speech (Table III). It can also be seen that neuro-psychological manifestations of Parkinson's disease disappeared completely within six months from commencing treatment. The reduction in the UPDRS II tests in the "off" period and in the "on" period are also clearly to be seen (Table IV).

This treatment must not be interrupted and the doses must be constantly maintained at between 93 mg and 160 mg per day. Depending on the clinical improvement in each patient, the daily nicotine dose can be reduced or increased (but never decreased below 93 mg per day). Nicotine can be used for life depending on clinical evolution and the patient's symptoms.

EXAMPLE 3

Administration of Nicotine in Doses in the Range 0.2 to 5 mg Per Day Per Kilo Using a Pump and By Sub-Cutaneous Administration a) Administration using extracorporal pump:
An extracorporal pump, preferably portable, was used. A sub-cutaneous catheter enabled the required dose of nicotine to be administered permanently, which dose could be adjusted by a battery-driven variable speed governor.

b) Administration by rapid and slow release patches:
Patch administration or a transcutaneous pump must be positioned in locations where the nicotine is absorbed in an optimum manner and continuously to obtain an effective sanguine dose. These locations are preferably the buttocks or the lumbar cavities.

In conclusion, comparing the results obtained with the drug of the invention, administered together with L-DOPA in sub-active doses, it appears that, for the first time, patients experience a re-establishment, reduction or complete stop to syndromes characterizing Parkinson's disease and associated diseases. The results of the UPDRS I, II and III tests also show clear re-establishment of dopaminergic and nicotinergic functions which allows long-term stabilization of these improvements to be presumed.

What is claimed is:

1. A drug composition for administration to a subject orally, subcutaneously, transdermally or any combination thereof, comprising as a first component, nicotine or a nicotine derivative, wherein said nicotine or nicotine derivative is present in an amount sufficient to be administered to said subject at a gradually increasing rate of from 0.2 mg to 5 mg per day per kilogram of body weight of said subject and a second component comprising L-DOPA in a dose at least 30% lower than the effective dose when L-DOPA is administered in the absence of said first component.

2. The drug composition of claim 1 wherein said second component further comprises a dopaminergic agonist.

3. The drug composition of claim 2 wherein said dopaminergic agonist is selected from the group consisting of bromocriptine and piribedil.

4. The drug composition of claim 1 wherein at least one of said components is in galenical form.

5. A method for improving the functionality of D1 and D2 dopaminergic receptors associated with neurodegenerative diseases, multi-systemic atrophies or both, comprising administering to a human mammal over a long term period an effective dose of at least two drug components comprising a first component nicotine or a nicotine derivative in an amount sufficient to be administered to said human mammal at a rate from 0.2 mg to 5 mg per day per kilogram of body weight, and a second component comprising L-DOPA in a dose at least 30% lower than the effective dose when L-DOPA is administered in the absence of said first component and a dopaminergic agonist.

6. The method of claim 5, wherein said D1 and D2 dopaminergic receptors are associated with neurodegenerative diseases.

7. The method of claim 6 wherein said neurodegenerative diseases are selected from the group consisting of Parkinson's disease and Tourette's syndrome.

8. The method of claim 5, wherein said dopaminergic agonist is bromocriptine or piribedil.

9. The method of claim 5, wherein said two drug components are administered transdermally, subcutaneously, by using an extracorporeal pump, or orally.

10. The method of claim 9 wherein at least one of said components is in galenical form.

11. The method of claim 5, wherein said first component is administered at a gradually increasing rate.

12. The method of claim 5 wherein the term of said long period is at least about four months.

13. A method for treating a neurodegenerative disease, a multi-systemic atrophy, or both, in a human mammal comprising administering to said human mammal over a long term period an effective dose of at least two drug components comprising as a first component, nicotine or a nicotine derivative, wherein said nicotine or nicotine derivative is present in an amount sufficient to be administered to said human mammal at a gradually increasing rate of from 0.2 mg to 5 mg per day per kilogram of body weight of said human mammal and a second component comprising L-DOPA in a dose at least 30% lower than the effective dose when L-DOPA is administered in the absence of said first component and a dopaminergic agonist.

14. The method of claim 13 wherein said dopaminergic agonist is bromocriptine or piribedil.

15. The method of claim 14 wherein said treatment enables multiplication, stimulation and increase of nicotinergic receptors and pre-synaptic and post-synaptic D1 and D2 receptors in the nigrostriatum zone.

16. The method of claim 13 wherein said two drug components are administered transdermally, subcutaneously, by using an extracorporeal pump or orally.

17. The method of claim 13 wherein at least one of said drug components is in galenical form.

18. The method of claim 13 wherein the term of said long period is at least about four months.

19. The method of claim 5 wherein said administering is continuous or in doses which increase over three consecutive months followed by stabilized doses after three months.

20. The method of claim 19 wherein said nicotine or nicotine derivative is administered at a rate of from 93 mg to 160 mg per day.

21. The method of claim 19 wherein said nicotine or nicotine derivative is administered at a rate of 0.2 mg to 5 mg per day per kg of body weight of said human mammal, and wherein said L-DOPA is administered at a rate of 0.2 mg to 3 mg per day per kg of body weight of said human mammal.

22. The method of claim 5 or claim 13 wherein said administration of said first component at a gradually increasing rate is accompanied by a concomitant reduction in the L-DOPA dose.

23. The method of claim 13, wherein said administering is continuous or in doses which increase over three consecutive months followed by stabilized doses after three months.

24. The method of claim 23, wherein said nicotine or nicotine derivative is administered at a rate of from 93 mg to 160 mg per day.

25. The method of claim 23, wherein said nicotine or nicotine derivative is administered at a rate of 0.2 mg to 5 mg per day per kg of body weight of said human mammal, and wherein said L-DOPA is administered at a rate of 0.2 mg to 3 mg per day per kg of body weight of said human mammal.

26. A drug composition for continuous administration and/or administration in doses which increase over three consecutive months followed by stabilized doses after three months to a subject orally, subcutaneously, transdermally or any combination thereof comprising as a first component, nicotine or a nicotine derivative, wherein said nicotine or nicotine derivative is present in an amount sufficient to be administered to said human mammal at a rate of from 0.2 mg to 5 mg per day per kilogram of body weight of said subject and a second component comprising L-DOPA in a dose of 0.2 mg to 3 mg per day per kilogram weight of said subject and a dopaminergic agonist.

27. The drug composition of claim 26, wherein said dopaminergic agonist is selected from the group consisting of bromocriptine and piribedil.

28. The drug composition of claim 1 or claim 26 wherein said nicotine or said nicotine derivative is present in an amount sufficient to be administered to said subject at a rate of from 93 mg to 160 mg per day.

29. The drug composition of claim 1 or claim 26 wherein said L-DOPA is present in an amount sufficient to be administered to a subject at a rate of 0.2 mg to 3 mg per day per kilogram of body weight of said subject.

* * * * *

UNITED STATES PATENT AND TRADEMARK OFFICE
CERTIFICATE OF CORRECTION

PATENT NO. : 6,911,475 B1
DATED : June 28, 2005
INVENTOR(S) : Villafane et al.

It is certified that error appears in the above-identified patent and that said Letters Patent is hereby corrected as shown below:

Title page, Item [54] and Column 1, lines 1-4,
Title, "USE OF NICOTINE OR ITS DERIVATIVES IN A DRUG FOR TREATING NEUROLOGICAL DISEASE, IN PARTICULAR PARKINSON'S DISEASE" should read -- USE OF NICOTINE OR DERIVATIVE THEREOF FOR THE TREATMENT OF NEUROLOGIC DISEASES, IN PARTICULAR PARKINSON DISEASE --.

Title page,
Item [75], Inventors, "Pierre Cesaro, Saint-Maurice (FR); Gabriel Villafane, Paris (FR)" should read -- Gabriel Villafane, Paris (FR); Pierre Cesaro, Saint-Maurice (FR) --.

Signed and Sealed this

Twenty-fifth Day of October, 2005

JON W. DUDAS
*Director of the United States Patent and Trademark Office*